US00PP22170P2

(12) United States Plant Patent
Hurd

(10) Patent No.: US PP22,170 P2
(45) Date of Patent: Sep. 27, 2011

(54) ***MONARDA* PLANT NAMED 'PARDON MY PURPLE'**

(50) Latin Name: *Monarda didyma*
Varietal Denomination: Pardon My Purple

(75) Inventor: Kevin A. Hurd, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 12/803,661

(22) Filed: Jul. 1, 2010

(51) Int. Cl.
*A01H 5/00* (2006.01)

(52) U.S. Cl. ..... Plt./455

(58) Field of Classification Search ..... Plt./455
See application file for complete search history.

*Primary Examiner* — Annette Para

(57) ABSTRACT

The new and distinct cultivar of ornamental cultivar of ornamental Bee Balm named *Monarda didyma* 'Pardon My Purple' has short, compact, branching stems, numerous dark fuchsia flowers and resistance to powdery mildew.

1 Drawing Sheet

Botanical classification: *Monarda didyma.*
Variety denomination: 'Pardon My Purple'.

BACKGROUND OF THE INVENTION

The present invention relates to the new and distinct cultivar of Bee Balm, botanically known as *Monarda didyma* 'Pardon My Purple', and hereinafter also referred to solely as the cultivar 'Pardon My Purple' or the "new plant". The new plant was hybridized in 2006 and separated out for further evaluation in the summer of 2007 by Kevin A. Hurd in the trial gardens fields of a Zeeland, Mich., USA, as a planned hybrid cross of *Monarda didyma* 'ACrade' U.S. Plant Pat. No. 19,580 more commonly known as 'Grand Parade' as the female or seed parent and *Monarda didyma* 'AChall' U.S. Plant Pat. No. 19,582 more commonly known as 'Grand Marshall' as the male or pollen parent. The plant has been asexually propagated by stem cuttings at the same nursery in the greenhouses in Zeeland, Mich., and subsequent asexually propagated plants found to be identical to the original selection.

BRIEF SUMMARY OF THE PLANT

*Monarda didyma* 'Pardon My Purple' is unique from all other Bee Balm known to the inventor. The nearest comparison varieties are the two parents. In comparison, both 'AChall' and 'ACrade' are taller and have more purple and less red flowers.

The following are traits of *Monarda didyma* 'Pardon My Purple' that in combination distinguish it from all other Bee Balm known to the inventor:

1. Short habit
2. Dark green powdery mildew resistant foliage.
3. Compact dark fuchsia flowers for a long period in summer.

BRIEF DESCRIPTION OF THE DRAWINGS

The photographs of the new plant demonstrate the unique traits of 'Pardon My Purple' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
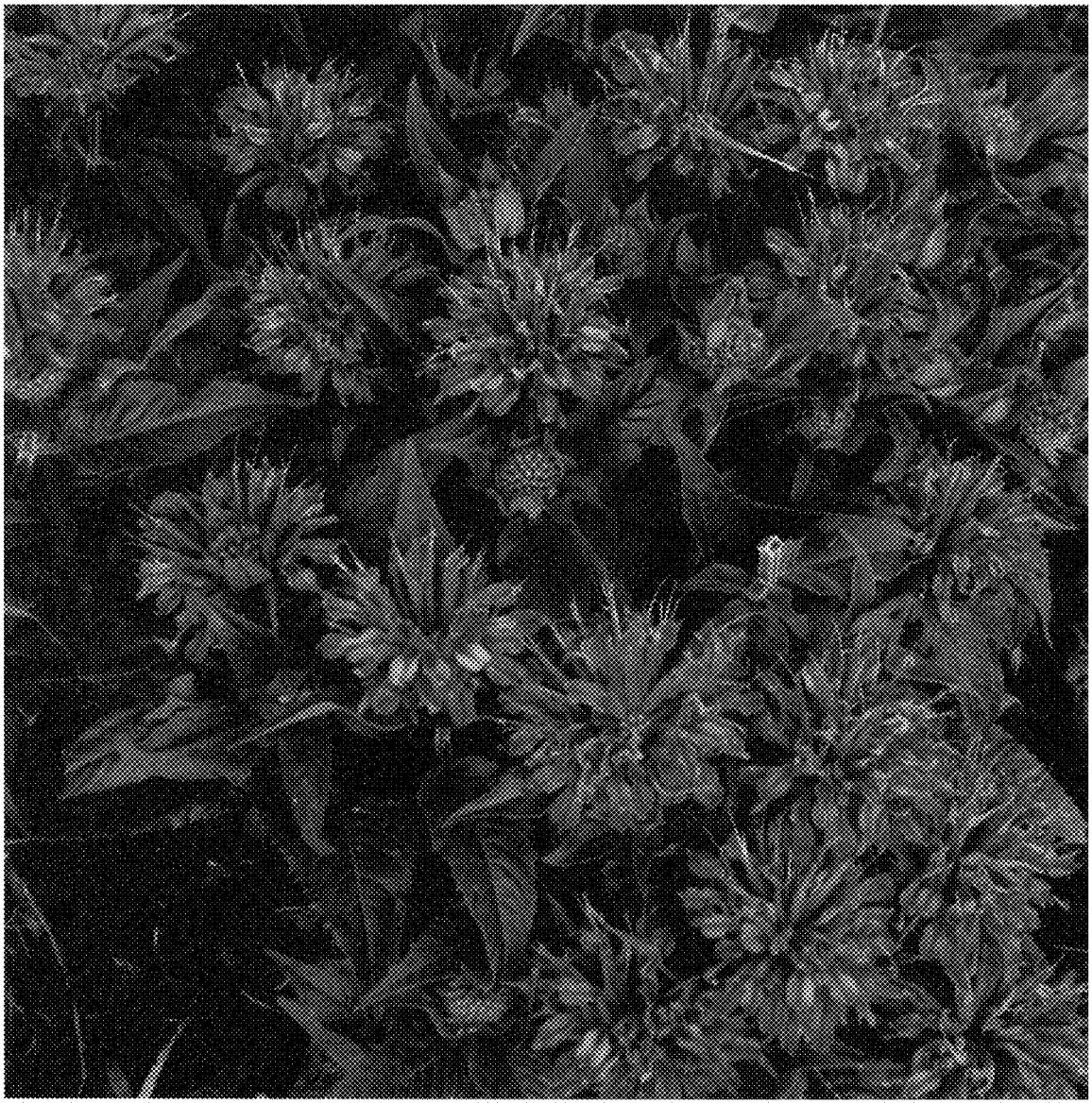
FIG. 1 shows the new plant in flower.

The following descriptions and color references are based on the 2001 edition of The Royal Horticultural Society Colour Chart except where common dictionary terms are used. *Monarda didyma* 'Pardon My Purple' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Monarda didyma;*

Parentage: Female (seed) parent is *Monarda didyma* 'ACrade' U.S. Plant Pat. No. 19,580; male (pollen) parent is *Monarda didyma* 'AChall' U.S. Plant Pat. No. 19,582;

Plant habit: Hardy herbaceous perennial, compact, producing several stems spreading by rhizomes; 25 to 30 cm tall at flowering and 18 to 24 cm wide; flowering begins midsummer in Michigan and continuing for about 8 weeks;

Propagation: Stem cuttings;

Time to produce finished crop in 3.8 liter pots: About 8 to 10 weeks; moderate rate of growth;

Root: Fine, fibrous and freely branching; color creamy white to tan depending on soil type;

Leaves: Simple, lanceolate, opposite, serrated, minutely pubescent above and below; acute apex, obtuse to cordate base; 5 to 7 cm long by 2.2 to 2.7 cm wide, nearest RHS 135A on top, between RHS 139B and RHS 137B below; lustrous above, dull beneath; pubescent both surfaces;

Foliage fragrance: Pleasantly spicy;

Veins: Pinnate; pubescent below with minute pubescence above, slightly sunken above and raised below; RHS 135A developing to nearest RHS 185B on top with sunlight, and underneath nearest RHS 147C;

Petiole: Pubescent, slightly concaved, about 8.0 mm long and 1.5 mm across; nearest RHS 185B on top with sunlight and nearest RHS 147C underneath;

Flowers: Single labiate flowers arranged in terminal globular head about 8.0 cm across and 2.4 cm tall opening from the center and progressing outwardly and down; persisting about 5 days in Michigan; numerous, about 250 flowers per head;

Flower fragrance: Moderately spicy;

Buds one to two days prior to opening: Narrowly oblanceolate, curved downward; about 2.0 cm long and 3 mm diameter; RHS 71A with a base of white, lighter than RHS N155D; Petals; labiate and split in two in the proximal 1.2 cm with upper lip fused into a hood about 3.0 cm long and 2.5 mm diameter; lower lip comprising three lobes fused until the distal 3.0 to 4.0 mm and then splitting into three lobes with the center lobe split in the distal 1.0 mm; both lobes glandular and pubescent outer surfaces with fine hairs the same color as petals; self-cleaning;

Petal color: Color of all petals on both surfaces RHS 71A with basal 5.0 mm white, lighter than RHS 11A;

Filaments: Two, about 3.2 cm long m by 0.5 mm diameter; nearest RHS N74C;

Anther: Oblong elliptic, 2.0 mm by 0.5 mm nearest RHS 176A;

Pollen: Abundant, elliptic to globose, less than 0.1 mm; nearest RHS 19D;

Pistil: One per flower;

Style: 3.3 mm by 0.25 mm; nearest RHS 72B at distal end and RHS N74D at proximal end;

Stigma: Split in the proximal 2 mm, 0.25 mm in diameter; RHS 72B;

Ovary: 1.0 mm by 0.75 mm, between RHS 143D and RHS 144B;

Sepals: Five, apiculate apex, base fused forming corolla about 8.0 mm long and 2.0 mm diameter; sepal apex color nearest RHS 177A, proximal glandular and with minute hairs on outer surface; distal half of outer corolla surface nearest RHS 147D with darker stripes of RHS 147C; proximal half of outer corolla surface lighter than RHS 145D without stripes; inner surfaces same color as outer;

Peduncle: Pubescent, stiff, strong, erect, squared to about 0.5 cm across and 25 cm long; nearest RHS 138A with a slight magenta tinting; about 20 per plant; branched at each node; about 2.0 cm between nodes;

Fruit: Fruit and see have not yet been observed;

Hardiness, pest and disease resistance: The new plant grows best with plenty of moisture and adequate drainage; hardy to at least from USDA zone 4 through 8.

Disease and pest resistance: Demonstrated powdery mildew resistance in side by side comparison approximately equal that of 'ACrade' and better than 'AChall' and 'Pink Lace' U.S. Plant Pat. No. 18,367.

I claim:

1. A new and distinct cultivar of ornamental Bee Balm, *Monarda didyma* 'Pardon My Purple', as herein described and illustrated, with short compact stems, numerous dark fuchsia flowers and resistance to powdery mildew especially suitable as a potted plant, for the garden, and for cut flower arrangements.

* * * * *